United States Patent [19]

Hubele et al.

[11] 4,143,155
[45] Mar. 6, 1979

[54] SULFONYLGLYCOLIC ANILIDE FUNGICIDES

[75] Inventors: Adolf Hubele, Magden, Switzerland; Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 832,752

[22] Filed: Sep. 12, 1977

[30] Foreign Application Priority Data

Sep. 17, 1976 [CH]  Switzerland ............... 11816/76
Aug. 4, 1977 [CH]  Switzerland ............... 9580/77

[51] Int. Cl.² ............... A61K 31/255; A61K 31/335; C07C 143/68; C07D 307/32
[52] U.S. Cl. ............... 424/303; 260/456 A; 260/455 R; 260/343.6; 424/301; 424/279
[58] Field of Search ............... 260/456 A; 424/303; 560/250

[56] References Cited

U.S. PATENT DOCUMENTS

| | | | |
|---|---|---|---|
| 3,536,721 | 10/1970 | Soong et al. | 260/456 A |
| 3,849,467 | 11/1974 | Mangold et al. | 260/456 A |
| 3,954,827 | 5/1976 | Fischer et al. | 260/456 A |
| 3,960,919 | 6/1976 | Rohr et al. | 260/456 A |

*Primary Examiner*—Nicky Chan
*Attorney, Agent, or Firm*—Harry Falber

[57] ABSTRACT

Compounds of the formula I

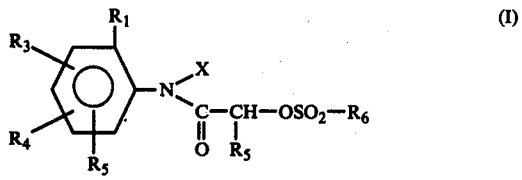

wherein
$R_1$ represents $C_1$–$C_4$ alkyl, $C_1$–$C_4$ alkoxy or halogen,
$R_2$ represents hydrogen, $C_1$–$C_3$ alkyl, $C_1$–$C_4$ alkoxy or halogen,
$R_3$ represents hydrogen, $C_1$–$C_3$ alkyl or halogen, and
$R_4$ represents hydrogen or methyl, with the proviso that the total number of carbon atoms contained by the substituents $R_1$, $R_2$, $R_3$ and $R_4$ does not exceed 8, X represents

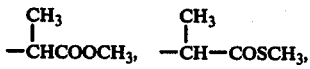 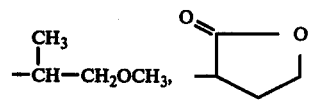

and
$R_5$ represents hydrogen or methyl and
$R_6$ represents $C_1$–$C_6$ alkyl which is unsubstituted or substituted by halogen or represents $C_2$–$C_4$ alkenyl or $C_3$–$C_6$ cycloalkyl or the group —N($R_7$)$R_8$, in which $R_7$ represents hydrogen or $C_1$–$C_4$ alkyl and $R_8$ represents $C_1$–$C_6$ alkyl which is unsubstituted or substituted by halogen, which are useful in combatting microorganisms in particular phytopathogenic fungi.

24 Claims, No Drawings

SULFONYLGLYCOLIC ANILIDE FUNGICIDES

The present invention relates to compounds of the formula I $$\text{(I)}$$

wherein
- $R_1$ represents $C_1$–$C_4$-alkyl, $C_1$–$C_4$-alkoxy or halogen,
- $R_2$ represents hydrogen, $C_1$–$C_3$-alkyl, $C_1$–$C_4$-alkoxy or halogen,
- $R_3$ represents hydrogen, $C_1$–$C_3$-alkyl or halogen, and
- $R_4$ represents hydrogen or methyl, with the proviso that the total number of carbon atoms contained by the substituents $R_1$, $R_2$, $R_3$ and $R_4$ does not exceed 8,
- X represents $$-\underset{\underset{\text{CH}_3}{|}}{\text{CH}}\text{COOCH}_3, \quad -\underset{\underset{\text{CH}_3}{|}}{\text{CH}}-\text{COSCH}_3,$$

$$-\underset{\underset{\text{CH}_3}{|}}{\text{CH}}-\text{CH}_2\text{OCH}_3,$$

and
- $R_5$ represents hydrogen or methyl and
- $R_6$ represents $C_1$–$C_6$-alkyl which is unsubstituted or substituted by halogen; $C_2$–$C_4$-alkenyl or $C_3$–$C_6$-cycloalkyl or represents the group $-N(R_7)R_8$, in which $R_7$ represents hydrogen or $C_1$–$C_4$-alkyl and $R_8$ represents $C_1$–$C_6$-alkyl which is unsubstituted or substituted by halogen, to a process for the manufacture of these compounds, to a method of controlling pests which comprises the use thereof and to compositions which contain said compounds as active ingredients.

By alkyl or as alkyl moiety of an alkoxy group are meant the following groups, depending on the stated number of carbon atoms: methyl, ethyl, propyl, butyl, pentyl or hexyl and the isomers thereof, for example isopropyl, isobutyl, sec-butyl, tert-butyl or isopentyl.

Suitable $C_2$–$C_4$-alkenyl groups are for example vinyl, allyl and 2-butenyl.

$C_3$–$C_6$-cycloalkyl groups are cyclopropyl, cyclobutyl, cyclopentyl and cyclohexyl. Halogen denotes fluorine, chlorine, bromine or iodine.

The compounds of the formula I can be obtained by reacting a compound of the formula II $$\text{(II)}$$

wherein $R_1$ to $R_5$ and X are as defined in formula I and Me represents hydrogen or an alkali metal ion or an alkaline earth metal ion, with a compound of the formula III $$\text{Hal SO}_2\text{R}_6 \quad \text{(III)}$$

wherein $R_6$ is as defined in formula I and Hal represents halogen, preferably chlorine or bromine.

This reaction may be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ether and ethereal compounds, such as dialkyl ethers, dioxane, tetrahydrofurane; nitriles, such as acetonitrile; N,N-dialkylated amides, such as dimethyl formamide, dimethyl sulphoxide, and mixtures of such solvents.

If Me in formula III represents hydrogen, the process is carried out in the presence of an acid acceptor.

Suitable acid acceptors are for example: tertiary amines, such as triethylamine, dimethyl aniline; pyridine bases; inorganic bases, such as hydroxides and carbonates of alkali metals and alkaline earth metals, preferably sodium and potassium carbonate.

The reaction is preferably carried out at a temperature between $-40°$ and $180°$ C, preferably between $-20°$ and $60°$ C, and under normal pressure.

The starting materials of the formula II are obtained by methods which are known per se (see for example German Offenlegungsschrift No. 2,417,781), for example as illustrated in the following reaction scheme:

$$\longrightarrow \text{C-R}_9 + \text{Me'OCH}_3$$

$$\downarrow$$

$$\text{II}$$

wherein $R_1$ and $R_5$ and X are as defined above, Me' represents a metal atom, preferably an alkali metal ion or alkaline earth metal ion, and $R_9$ represents a hydrocarbon radical, for example $C_1$–$C_4$-alkyl or phenyl.

The compounds of the formula I contain two possible asymmetrical carbon atoms which are in the positions 1 and 2 in the following formula:

1* - always asymmetrical
2* - asymmetrical if $R_5$ represents methyl.

The compounds of the formula I can be obtained in conventional manner (for example using already separated starting materials) as optical antipodes. The different configurations of such a compound of the formula I very in the potency of their microbicidal action. The influence of further centres of asymmetry in the molecule and the atropisomerism about the phenyl —N<axis have little effect on the microbicidal action of the entire molecule. Provided no synthesis with the object of isolating pure isomers of the formula I or of their primary products is carried out, a product will normally occur as a mixture of isomers.

The compounds of the formula I possess for practical purposes a very advantageous microbicidal spectrum for protecting cultivated plants. Examples of cultivated plants within the scope of this invention are: cereals, maize, rice, vegetables, sugar-beet, soya, ground nuts, fruit trees, ornamentals, and in particular vines, hops, cucumber plants (cucumber, marrows, melons), solanaceae, such as potatoes, tobacco plants and tomatoes, and also banana, cocoa and natural rubber plants.

With the active compounds of the formula I it is possible to inhibit or destroy the fungi which occur in plants or parts of plants (fruit, blossoms, leaves, stems, tubers, roots) in these and also related crops of useful plants, and also to protect from attack by such fungi the parts of plants which grow later. The active compounds are effective against the phytopathogenic fungi which belong to the following classes: Ascomycetes (e.g. Erysiphaceae); Basidiomycetes, in particular rust fungi; fungi imperfecti (e.g. Moniliales e.g. Cercospora); and especially against the Oomycetes belonging to the class of the Phycomycetes, such as Phytophthora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

On account of their action, an interesting group of compounds comprises those compounds of the formula I in which $R_1$ represents methyl, $R_2$ represents methyl or chlorine in the 6-position, $R_3$ represents hydrogen, chlorine, bromine or methyl, and $R_4$ represents hydrogen or methyl.

Another interesting group of compounds of the formula I comprises those compounds in which X represents

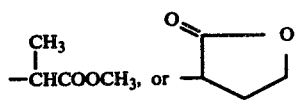

The substituent $R_6$ is preferably $C_1$-$C_4$-alkyl or the group $NHR_8$.

Preferred compounds within the groups of compounds referred to above are those in which $R_5$ is hydrogen.

Interesting compounds are also those of the formula I in which
 $R_1$ represents methyl or methoxy,
 $R_2$ represents methyl, ethyl or chlorine,
 $R_3$ represents hydrogen, methyl, chlorine or bromine,
 $R_4$ represents hydrogen or methyl,
 $R_5$ represents hydrogen and
 $R_6$ represents $C_1$-$C_6$-alkyl which is unsubstituted or substituted by chlorine, or represents vinyl, allyl, cyclohexyl or the group $N(R_7)R_8$, in which $R_7$ represents hydrogen, methyl or ethyl and $R_8$ represents methyl or ethyl which is unsubstituted or substituted by chlorine.

Similar compounds which contain a —$CH_2$—O—R group corresponding to the group X in formula I are described in German Offenlegungsschriften Nos. 2,349,256 and 2,417,764. Herbicidal activity is ascribed to these compounds, but no mention is made of a microbicidal action.

The compunds of the formula I can be used by themselves or together with suitable carriers and/or other additives. Suitable carriers and additives can be solid or liquid and correspond to the substances normally used in the art of formulation, for example natural or regenerated mineral substances, solvents, dispersants, wetting agents, tackifiers, thickeners, binders or fertilisers. The preparation of these compositions is effected in known manner by intimately mixing and grinding the constituents.

For application the active substances may be processed to the following formulations (in which the parts by weight refer to advantageous amounts of active substance):

Solid formulations:
 dusts, tracking agents, (up to 10%) granules (coated granules, impregnated granules and homogeneous granules); pellets (1 to 80%);

Liquid formulations:
 a. active substance concentrates which are dispersible in water: wettable powders, pastes: (25–90% in commercial packs, 0.01 to 15% in ready for use solutions emulsions; concentrated solutions (10 to 50%; 0.01 to 15% in ready for use solutions).
 b. Solutions, aerosols.

The content of active substance in the above described compositions is between 0.1% and 95% by weight.

It will be readily understood that the compounds of the formula I can be used together with other suitable pesticides, for example fungicides, insecticides, acaricides or active substances which influence plant growth, in order to adapt them to prevailing circumstances and to broaden the activity spectrum of the formulations.

The invention is illustrated by the following Examples, but without any restriction to what is described therein. Unless otherwise stated, a compound of the formula I is always to be understood as meaning the racemic mixture of possible isomers.

Manufacturing Examples

EXAMPLE 1

Preparation of N-(1'-methoxycarbonylethyl)-N-(methylsulphonoxy-acetyl)-2,6-dimethylaniline of the formula

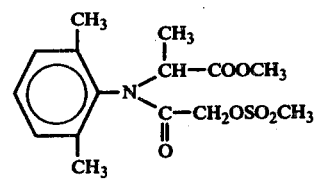

(compound 1)

With stirring, 26.5 g of N-(1'-methoxycarbonylethyl)-N-hydroxyacetyl-2,6-dimethylaniline and 8.7 g of pyridine in 150 ml of acetonitrile were treated dropwise at 5° C with 12.6 g of methanesulphochloride in 50 ml of acetonitrile. After stirring for 18 hours at room temperature, the reaction mixture was poured into 500 ml of water and extracted with three 150 ml portions of methylene chloride. The combined extracts were dried over sodium sulphate, filtered, and the solvent was evaporated off. The solid residue melts at 58°-61° C after crystallization from ether/petroleum ether (40°-60° C).

EXAMPLE 2

Preparation of N-(1'-methyl-2'-methoxyethyl)-N-(methylsulphonoxy-acetyl)-2,6-dimethylaniline of the formula

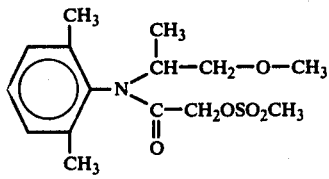

(compound 67)

With stirring, 25 g of N-(1'-methyl-2'-methoxyethyl)-N-hydroxyacetyl-2,6-dimethyaniline and 8.7 g of pyridine in 100 ml of acetonitrile were treated dropwise at 10° C with 12.6 g of methanesulphochloride in 60 ml of acetonitrile. After stirring for 16 hours at room temperature and for 30 minutes at 40° C, the reaction mixture was poured into 300 ml of water, extracted with three 100 ml portions of methylene chloride, dried over sodium sulphated and filtered. After evaporation of the solvent, the oily residue was distilled in a high vacuum at 134°–136° C and 0.06 torr.

The following compounds can be obtained by carrying out the procedure as described in the foregoing Examples or by one of the methods described above.

Table A $(X = CH(CH_3)-COOCH_3; R_5 = H)$

| Compound No. | $R_1$ | $R_2$ | $R_3$ | $R_4$ | $R_6$ | Physical constant (° C) |
|---|---|---|---|---|---|---|
| 1 | $CH_3$ | 6-$CH_3$ | H | H | $CH_3$ | mp. 58-61° |
| 2 | $CH_3$ | 6-$CH_3$ | H | H | $C_2H_5$ | b.p.165°/0.08 torr |
| 3 | $CH_3$ | 6-$CH_3$ | H | H | $C_3H_7(n)$ | b.p.180°/0.1 torr |
| 4 | $CH_3$ | 6-$CH_3$ | H | H | $C_3H_7(i)$ | |
| 5 | $CH_3$ | 6-$CH_3$ | H | H | $C_4H_9(n)$ | b.p.186–190°/0.1 torr |
| 6 | $CH_3$ | 6-$CH_3$ | H | H | $C_4H_9(s)$ | |
| 7 | $CH_3$ | 6-$CH_3$ | H | H | $C_6H_{13}(n)$ | |
| 8 | $CH_3$ | 6-$CH_3$ | H | H | $CH_2Cl$ | |
| 9 | $CH_3$ | 6-$CH_3$ | H | H | $CH=CH_2$ | |
| 10 | $CH_3$ | 6-$CH_3$ | H | H | —C$_6$H$_{11}$ | |
| 11 | $CH_3$ | 6-$CH_3$ | H | H | —$NHCH_3$ | $n_D^{20}$: 1.5375 |
| 12 | $CH_3$ | 6-$CH_3$ | H | H | —$N(CH_3)_2$ | |
| 13 | $CH_3$ | 6-$CH_3$ | H | H | —$N(C_2H_5)_2$ | |
| 14 | $CH_3$ | 6-$CH_3$ | H | H | —$N(CH_3)(C_2H_5)$ | |
| 15 | $CH_3$ | 6-$CH_3$ | H | H | —$N(CH_3)(CH_2CH_2Cl)$ | |
| 16 | $CH_3$ | 6-$CH_3$ | H | H | —$CH_2CH_2CH_2Cl$ | oil |
| 17 | $CH_3$ | 6-$CH_3$ | 3-$CH_3$ | H | $CH_3$ | m.p. 121-131° |
| 18 | $CH_3$ | 6-$CH_3$ | 3-$CH_3$ | H | $C_2H_5$ | |
| 19 | $CH_3$ | 6-$CH_3$ | 3-$CH_3$ | H | $C_3H_7(n)$ | |
| 20 | $CH_3$ | 6-$CH_3$ | 3-$CH_3$ | H | —$NHCH_3$ | |
| 21 | $CH_3$ | 6-$CH_3$ | 3-$CH_3$ | H | —$N(CH_3)_2$ | |
| 22 | $CH_3$ | 6-$CH_3$ | 3-$CH_3$ | 5-$CH_3$ | —$CH_3$ | |
| 23 | $CH_3$ | 6-$CH_3$ | 3-$CH_3$ | 5-$CH_3$ | —$C_2H_5$ | |
| 24 | $CH_3$ | 6-$CH_3$ | 3-$CH_3$ | 5-$CH_3$ | —$C_4H_9(n)$ | |
| 25 | $CH_3$ | 6-$CH_3$ | 3-$CH_3$ | 5-$CH_3$ | —$NHCH_3$ | |
| 26 | $CH_3$ | 6-$CH_3$ | 3-Cl | H | —$CH_3$ | |
| 27 | $CH_3$ | 6-$CH_3$ | 3-Cl | H | —$C_2H_5$ | |
| 28 | $CH_3$ | 6-$CH_3$ | 3-Cl | H | —$C_3H_7(n)$ | |
| 29 | $CH_3$ | 6-$CH_3$ | 3-Cl | H | —$NHCH_3$ | |
| 30 | $CH_3$ | 6-$CH_3$ | 4-Cl | H | —$CH_3$ | |
| 31 | $CH_3$ | 6-$CH_3$ | 4-Cl | H | —C$_6$H$_{11}$ | |
| 32 | $CH_3$ | 6-$C_2H_5$ | H | H | —$CH_3$ | |
| 33 | $CH_3$ | 6-$C_2H_5$ | H | H | —$NHCH_3$ | |
| 34 | $CH_3$ | 6-Cl | H | H | —$CH_3$ | |
| 35 | $CH_3$ | 6-Cl | H | H | —$C_2H_5$ | |
| 36 | $CH_3$ | 6-Cl | H | H | —$NHCH_3$ | |
| 37 | $OCH_3$ | 6-$CH_3$ | H | H | —$CH_3$ | |
| 38 | $CH_3$ | 6-$CH_3$ | 3-Br | H | —$CH_3$ | |
| 39 | $CH_3$ | 6-$CH_3$ | 4-Br | H | —$CH_3$ | |
| 40 | $CH_3$ | 6-$C_2H_5$ | 4-Br | H | —$CH_3$ | |
| 41 | $CH_3$ | 6-Br | 4-Cl | H | —$CH_3$ | |
| 42 | $CH_3$ | 6-$CH_3$ | H | H | —$CH_2$—$CH=CH_2$ | |
| 43 | $CH_3$ | 6-$CH_3$ | 3-$CH_3$ | 5-$CH_3$ | —$CH_2$—$CH=CH_2$ | |

Table B (X = 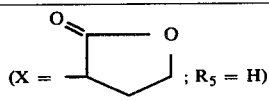 ; R$_5$ = H)

| Compound No. | R$_1$ | R$_2$ | R$_3$ | R$_4$ | R$_6$ | Physical constant °C |
|---|---|---|---|---|---|---|
| 44 | CH$_3$ | 6-CH$_3$ | H | H | CH$_3$ | m.p. 138–139° |
| 45 | CH$_3$ | 6-CH$_3$ | H | H | C$_2$H$_5$ | m.p. 119–121° |
| 46 | CH$_3$ | 6-CH$_3$ | H | H | C$_3$H$_7$(n) | |
| 47 | CH$_3$ | 6-CH$_3$ | H | H | C$_3$H$_7$(i) | m.p. 111–119° |
| 48 | CH$_3$ | 6-CH$_3$ | H | H | C$_4$H$_9$(n) | |
| 49 | CH$_3$ | 6-CH$_3$ | H | H | NHCH$_3$ | |
| 50 | CH$_3$ | 6-CH$_3$ | H | H | —CH=CH$_2$ | |
| 51 | CH$_3$ | 6-CH$_3$ | H | H | N(CH$_3$)$_2$ | |
| 52 | CH$_3$ | 6-CH$_3$ | H | H | —CH$_2$Cl | |
| 53 | CH$_3$ | 6-CH$_3$ | 3-CH$_3$ | H | —CH$_3$ | m.p. 116–118° |
| 54 | CH$_3$ | 6-CH$_3$ | 3-CH$_3$ | H | —C$_2$H$_5$ | |
| 55 | CH$_3$ | 6-CH$_3$ | 3-CH$_3$ | H | —C$_3$H$_7$(n) | |
| 56 | CH$_3$ | 6-CH$_3$ | 3-CH$_3$ | H | —NHCH$_3$ | |
| 57 | CH$_3$ | 6-CH$_3$ | 3-CH$_3$ | 5-CH$_3$ | —CH$_3$ | |
| 58 | CH$_3$ | 6-CH$_3$ | 3-CH$_3$ | 5-CH$_3$ | —C$_2$H$_5$ | |
| 59 | CH$_3$ | 6-CH$_3$ | 3-CH$_3$ | 5-CH$_3$ | —NHCH$_3$ | |
| 60 | CH$_3$ | 6-CH$_3$ | 3-Cl | H | —CH$_3$ | |
| 61 | CH$_3$ | 6-CH$_3$ | 3-Cl | H | —NHCH$_3$ | |
| 62 | CH$_3$ | 6-Cl | H | H | —CH$_3$ | |
| 63 | CH$_3$ | 6-Cl | H | H | NHCH$_3$ | |
| 64 | CH$_3$ | 6-C$_2$H$_5$ | H | H | —CH$_3$ | |
| 65 | CH$_3$ | 6-CH$_3$ | 4-Cl | H | —CH$_3$ | |
| 66 | OCH$_3$ | 6-CH$_3$ | H | H | —CH$_3$ | |

Table C (X = —CH(CH$_3$)CH$_2$OCH$_3$ ; R$_5$ = H)

| Compound No. | R$_1$ | R$_2$ | R$_3$ | R$_4$ | R$_6$ | Physical constant °C |
|---|---|---|---|---|---|---|
| 67 | CH$_3$ | 6-CH$_3$ | H | H | —CH$_3$ | b.p.$_{20}$ 134–136° |
| 68 | CH$_3$ | 6-CH$_3$ | H | H | C$_4$H$_9$(n) | n$_D^{20}$: 1,5085 |
| 69 | CH$_3$ | 6-CH$_3$ | H | H | NHCH$_3$ | |
| 70 | CH$_3$ | 6-CH$_3$ | 3-CH$_3$ | H | —CH$_3$ | n$_D^{20}$: 1,5189 |
| 71 | CH$_3$ | 6-CH$_3$ | 3-CH$_3$ | H | NHCH$_3$ | |
| 72 | CH$_3$ | 6-CH$_3$ | 3-CH$_3$ | 5-CH$_3$ | —CH$_3$ | |
| 73 | CH$_3$ | 6-CH$_3$ | 3-Cl | H | —CH$_3$ | |
| 74 | CH$_3$ | 6-Cl | H | H | —CH$_3$ | |

Table D (X = —CH(CH$_3$)—COSCH$_3$ ; R$_5$ = H)

| Compound No. | R$_1$ | R$_2$ | R$_3$ | R$_4$ | R$_6$ |
|---|---|---|---|---|---|
| 75 | CH$_3$ | 6-CH$_3$ | H | H | CH$_3$ |
| 76 | CH$_3$ | 6-CH$_3$ | H | H | C$_2$H$_5$ |
| 77 | CH$_3$ | 6-CH$_3$ | H | H | NHCH$_3$ |

Table E

| Compound No. | R$_1$ | R$_2$ | R$_3$ | R$_4$ | X | R$_6$ |
|---|---|---|---|---|---|---|
| 78 | CH$_3$ | 6-CH$_3$ | H | H | —CH(CH$_3$)COOCH$_3$ | CH$_3$ |
| 79 | CH$_3$ | 6-CH$_3$ | H | H | 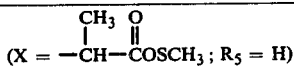 | CH$_3$ |
| 80 | CH$_3$ | 6-CH$_3$ | H | H | —CH(CH$_3$)CH$_2$OCH$_3$ | CH$_3$ |

Biological Examples

EXAMPLE 3

Action against Cercospora arachidicola on ground nut plants

Three-week-old ground nut plants were sprayed with a spray broth (containing 0.02% of active substance) prepared from a wettable powder of the active substance. After approx. 12 hours the treated plants were infected by dusting with a conidia suspension of the fungus. The infected plants were then incubated for approx. 24 hours at 90% relative humidity and then stood in a greenhouse at approx. 22° C. The fungus attack was evaluated after 12 days.

EXAMPLE 4

Action against Phytophthora infestans on tomatoes (a) Curative Action

"Rotor Gnom" tomato plants were sprayed when 3 weeks old with a zoospore suspension of the fungus and incubated in a climatic chamber at 18° to 20° C and saturated humidity. The humidifying was interrupted after 24 hours. After the plants had dried, they were sprayed with a broth containing the active substance formulated as a wettable powder in a concentration of 0.06%. After the spray coating had dried, the plants were again kept in the humid chamber for 4 days. The effectiveness of the tested substances was assessed by determining the size and number of the typical leaf speck which had occured during this time.

(b) Preventive-systemic action

The active substance formulated as a wettable powder was applied in a concentration of 0.006% (referred to the volume of the soil) to the surface of the soil of 3-week-old "Rotor Gnom" tomatoes in pots. Three days later the underside of the leaves of the plants was sprayed with a zoospore suspension of Phytophthora infestans. The plants were then kept in a spray chamber at 18° to 20° C and saturated humidity for 5 days, after which time typical leaf specks formed. The effectiveness of the tested substance was assessed by determining the size and number of the specks.

EXAMPLE 5

Action against Piricularia oryzae on rice (A) Residual protective action

Two-week-old rice plants were sprayed with a spray broth (containing 0.02% of active substance) prepared from a wettable powder of the active substance. The treated plants were infected 48 hours later with a conidia suspension of the fungus. The fungus attack was evaluated after the plants had been incubated for 5 days at 95-100% relative humidity and 24° C.

(b) Systemic action

Two-week-old rice plants were sprayed with a spray broth (containing 0.006% of active substance, referred to the volume of the soil) prepared from a wettable powder of the active substance. The pots were then filled with water until the lowest parts of the stems of the rice plants were covered. The treated rice plants were infected 48 hours later with a conidia suspension of the fungus. The fungus attack was evaluated after the infected plants had been incubated for 5 days at 95-100% relative humidity and 24° C.

EXAMPLE 6

Action on Pythium debaryanum on sugar beets

The fungus was cultivated on sterile oat grains and added to a mixture of earth and sand. Flower pots were filled with the infected soil in which sugar beet seeds were then sown. Immediately after sowing, the test preparations formulated as wettable powders were poured in the form of aqueous suspensions over the soil (20 ppm of active substance referred to the volume of the soil). The pots were then stood for 2-3 weeks in a greenhouse at 20°-24° C. The soil was kept uniformly moist by gently spraying it with water. The emergence of the sugar beet plants as well as the number of healthy and sick plants were determined in evaluating the tests.

The following compounds effected an inhibition of attack by the following fungi to less than 20% compared with control plants:

| | |
|---|---|
| *Cercospoa arachidicola* | - compound 11 |
| *Phytophthora infestans* | - compounds 1, 11, 16, 17, 44 and 53 |
| *Plasmopara viticola* | - compund 1 |
| *Pythium debarynum* | - compounds 1, 11, 17, 44 and 53. |

Formulation Examples

EXAMPLE 7

Dusts: The following substances are used to prepare
(a) 5% and
(b) a 2% dust:
(a) 5 parts of active subtance, 95 parts of talc;
(b) 2 parts of active substance, 1 part of highly dispersed silicic acid, 97 parts of talc.

The active substances are mixed with the carriers and ground and in this form can be processed to dusts for application.

EXAMPLE 8

Granulate: The following substances are used to prepare a 5% granulate:

5 parts of active substances
0.25 part of epichlorohydrin
0.25 part of cetyl polyglycol ether
3.25 parts of polyethylene glycol
91 parts of kaolin (particle size 0.3 - 0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combating soil fungi.

EXAMPLE 9

Wettable powders: The following constituents are used to prepare (a) a 70%, (b) a 40%, (c) and (d) a 25% and (e) a 10% wettable powder:

(a)

70 parts of active substance
5 parts of sodium dibutylnaphthylsulphonate
3 parts of naphthalenesulphonic acid/phenolsulphonic acid/formaldehyde condensate (3:2:1)
10 parts of kaolin
12 parts of Champagne chalk (b)

40 parts of active substance
5 parts of sodium ligninsulphonate
1 part of sodium dibutylnaphthalenesulphonic acid
54 parts of silicic acid (c)

25 parts of active substance
4.5 parts of calcium ligninsulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)

25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

EXAMPLE 10

Emulsifiable concentrates: The following substances are used to prepare a 25% emulsifiable concentrate:

25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

What is claimed is:

1. A compound of the formula I

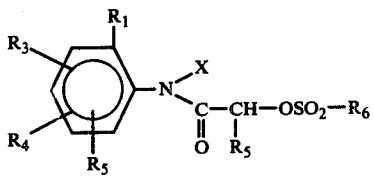

wherein
R₁ represents C₁-C₄ alkyl, C₁-C₄ alkoxy or halogen,
R₂ represents hydrogen, C₁-C₃ alkyl, C₁-C₄ alkoxy or halogen,
R₃ represents hydrogen, C₁-C₃ alkyl or halogen, and
R₄ represents hydrogen or methyl, with the proviso that the total number of carbon atoms contained by the substituents R₁, R₂, R₃ and R₄ does not exceed 8,
X represents

R₅ represents hydrogen or methyl and
R₆ represents C₁-C₆ alkyl which is unsubstituted or substituted by halogen or represents C₂-C₄ alkenyl or C₃-C₆ cycloalkyl or the group —N(R₇)R₈, in which R₇ represents hydrogen or C₁-C₄ alkyl and R₈ represents C₁-C₆ alkyl which is unsubstituted or substituted by halogen.

2. A compound according to claim 1 wherein R₁ represents methyl, R₂ represents methyl or chlorine in the 6-position, R₃ represents hydrogen, chlorine, bromine or methyl and R₄ represents hydrogen or methyl.

3. A compound according to claim 1 wherein R₆ represents C₁-C₄ alkyl or the group NHR₈.

4. A compound according to claim 1 wherein R₅ represents hydrogen.

5. A compound according to claim 1 wherein
R₁ represents metyl or methoxy,
R₂ represents methyl, ethyl or chlorine,
R₃ represents hydrogen, methyl, chlorine or bromine,
R₄ represents hydrogen or methyl,
R₅ represents hydrogen and
R₆ represents C₁-C₆-alkyl which is unsubstituted or substituted by halogen, or represents vinyl, allyl, cyclohexyl or the group N(R₇)R₈ in which R₇ represents hydrogen, methyl or ethyl and R₈ represents methyl or ethyl which is unsubstituted or substituted by chlorine.

6. A compound according to claim 2 wherein
R₅ represents hydrogen and
R₆ *represents* C₁-C₄ alkyl or the group NHR₈.

7. A compound according to claim 1 which is N-(1'-methoxycarbonylethyl)-N-(methylsulphonoxy-acetyl)-2,6-dimethylaniline.

8. A compound according to claim 1 selected from the group consisting of

N-(1'-methoxycarbonylethyl)-N-(ethylsulphonoxy-acetyl)-2,6-dimethylaniline,
N-(1'-methoxycarbonylethyl)-N-(n-propylsulphonoxy-acetyl)-2,6-dimethylaniline,
N-(1'-methoxycarbonylethyl)-N-(n-butylsulphonoxy-acetyl)-2,6-dimethylaniline,
N-(1'-methoxycarbonylethyl)-N-(methylaminosulphonoxy-acetyl)-2,6-dimethylaniline, and
N-(1'-methoxycarbonylethyl)-N-(methylsulphonoxy-acetyl)-2,3,6-trimethylaniline.

9. A phytopathogenic fungicidal composition containing as active ingredient a phytopathogenic fungicidally effective amount of a compound according to claim 1 together with a solid extender and optionally a surfactant or with a liquid diluent and a surfactant.

10. A phytopathogenic fungicidal composition containing as active ingredient a phytopathogenic fungicidally effective amount of a compound according to claim 2 together with a solid extender and optionally a surfactant or with a liquid diluent and a surfactant.

11. A phytopathogenic fungicidal composition containing as active ingredient a phytopathogenic fungicidally effective amount of a compound according to claim 3 together with a solid extender and optionally a surfactant or with a liquid diluent and a surfactant.

12. A phytopathogenic fungicidal composition containing as active ingredient a phytopathogenic fungicidally effective amount of a compound according to claim 4 together with a solid extender and optionally a surfactant or with a liquid diluent and a surfactant.

13. A phytopathogenic fungicidal composition containing as active ingredient a phytopathogenic fungicidally effective amount of a compound according to claim 5 together with a solid extender and optionally a surfactant or with a liquid diluent and a surfactant.

14. A phytopathogenic fungicidal composition containing as active ingredient a phytopathogenic fungicidally effective amount of a compound according to claim 6 together with a solid extender and optionally a surfactant or with a liquid diluent and a surfactant.

15. A phytopathogenic fungicidal composition containing as active ingredient a phytopathogenic fungicidally effective amount of a compound according to claim 7 together with a solid extender and optionally a surfactant or with a liquid diluent and a surfactant.

16. A phytopathogenic fungicidal composition containing as active ingredient a phytopathogenic fungicidally effective amount of a compound according to claim 8 together with a solid extender and optionally a surfactant or with a liquid diluent and a surfactant.

17. A method of combatting phytopathogenic fungi which comprises applying thereto or to the locus thereof an effective amount of a compound according to claim 1.

18. A method of combatting phytopathogenic fungi which comprises applying thereto or to the locus thereof an effective amount of a compound according to claim 2.

19. A method of combatting phytopathogenic fungi which comprises applying thereto or to the locus thereof an effective amount of a compound according to claim 3.

20. A method of combatting phytopathogenic fungi which comprises applying thereto or to the locus thereof an effective amount of a compound according to claim 4.

21. A method of combatting phytopathogenic fungi which comprises applying thereto or to the locus thereof an effective amount of a compound according to claim 5.

22. A method of combatting phytopathogenic fungi which comprises applying thereto or to the locus thereof an effective amount of a compound according to claim 6.

23. A method of combatting phytopathogenic fungi which comprises applying thereto or to the locus thereof an effective amount of a compound according to claim 7.

24. A method of combatting phytopathogenic fungi which comprises applying thereto or to the locus thereof an effective amount of a compound according to claim 8.

* * * * *

UNITED STATES PATENT AND TRADEMARK OFFICE
CERTIFICATE OF CORRECTION

PATENT NO. : 4,143,155

DATED : March 6, 1979

INVENTOR(S) : Adolf Hubele et al.

It is certified that error appears in the above-identified patent and that said Letters Patent are hereby corrected as shown below:

At Column 11, in Claim 1, the structural formula should appear as follows:

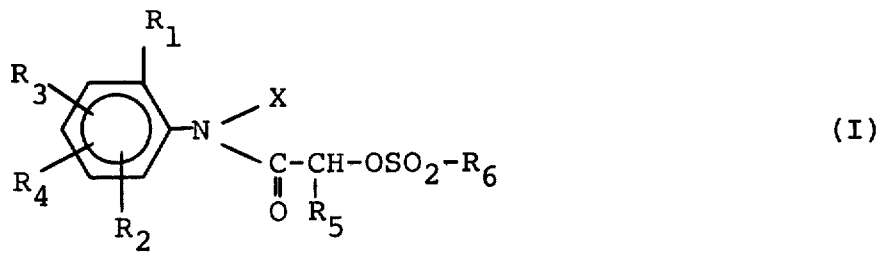

(I)

Signed and Sealed this

Twenty-ninth Day of May 1979

[SEAL]

Attest:

RUTH C. MASON
Attesting Officer

DONALD W. BANNER
Commissioner of Patents and Trademarks